United States Patent [19]

Lee

[11] Patent Number: 5,362,499
[45] Date of Patent: Nov. 8, 1994

[54] BURN REMEDIAL COMPOSITION USING NATURAL MATERIALS AND ITS PRODUCTION METHOD

[76] Inventor: Seung H. Lee, 332-12, Daeseong-Li, Oisuh-Meon, Kapyeong-Kun, Kyungki-Do 477-810, Rep. of Korea

[21] Appl. No.: 82,095

[22] Filed: Jun. 24, 1993

[30] Foreign Application Priority Data

Dec. 16, 1992 [KR] Rep. of Korea .................... 92-24472

[51] Int. Cl.$^5$ ............................................. A61K 35/12
[52] U.S. Cl. ............................ 424/547; 424/DIG. 13; 514/558
[58] Field of Search ............ 424/547, DIG. 13, 195.1; 514/558

[56] References Cited

U.S. PATENT DOCUMENTS 4,690,816  9/1987  Tittafa et al. ........................ 424/456

FOREIGN PATENT DOCUMENTS 53032108 of 0000 Japan .
252099912 of 0000 Japan .

*Primary Examiner*—John W. Rollins
*Attorney, Agent, or Firm*—Ladas & Parry

[57] ABSTRACT

This invention is a burn remedial composition which is produced by mixing powder of the high heated abalone shells with sesame oil extracted from sesame, and its production method wherein it is characteristic that the grinding process of abalone shells heated at a temperature higher than 3000° C. and the mixing process of the ground abalone shell powder and sesame oil are not performed in a stone or metallic vessel, but in a wooden vessel. A pharmaceutical additive can be added to aid the formation of a pharmaceutical type of burn remedial composition. When the burn remedial composition of the invention is applied to every degree of heat burn and fire burn for which there are few curing agents, especially to severe burns, the analgesic and antiphlogistic effects happen at that moment, the toxic materials in the injured region are eliminated within 24 hours and the injury is completely cured within 3-5 days. And, the burn remedy has the excellent effect of restoring the injury to near normal skin with little scar, and it has the same effect on burns as well as on various kinds of external wounds where there was skin damage.

8 Claims, No Drawings

BURN REMEDIAL COMPOSITION USING NATURAL MATERIALS AND ITS PRODUCTION METHOD

TECHNICAL FIELD

This invention relates to a composition using natural materials, which are very effective in curing burns, and provides its production method. It relates to a burn remedial composition which is characterized by having the excellent and rapid effects of curing all kinds of burns without pain and without remaining burn scars. More particularly, it relates to a composition which is a mixed powder of abalone shell treated by high temperature with oil extracted from parched sesames and which is effective to cure burns and similar kinds of injuries thereas, and provides its production method.

BACKGROUND ART

Burns are currently classified into four groups by the depth of injury. First degree burns, which damage the epidermis alone, cause erythema and edema. Second degree burns which damage the epidermis and a part of the mid-dermis, cause bullae. Third degree burns, which damage all layers of the dermis, cause eschars. The injury of third degree burns can not be naturally cured, and in some cases, it is necessary to graft some skin for eliminating scars. Fourth degree burns damage fat and muscles or bones through the dermis. Pain is prominent in first and second degree burns. The major complications of burns are pain, infections, metabolic derangements and scarring. Measures for treating burns include flooding with cool water, tetanus prophylaxis, antibiotic treatment and anticipation of shock with immediate intravenous fluid replacement. There are no special treatments for first degree burns except waiting for natural healing after flooding with cool water. For second and third degree burns the injuries are dressed with, sterilized gauze and some antibiotics are used including penicillin, erythromycin, sulfamine, etc., to prohibit infection. Some analgesics are taken for pain. However, there have been few remedies which can substantially heal and cure the burn wound. Moreover, it is impossible for usual burn treatment to completely cure severe burns in spite of a long treatment period and expensive cost. And, skin grafting has been necessary for most scars even after treating most severe burns.

DISCLOSURE OF INVENTION

The object of this invention is to provide a burn remedial composition which has antiphlogistic and analgesic effects and can completely cure the burn injury to recover the normal state, and provide its production method.

Additionally, the object of this invention is to provide a burn remedial composition which inapplicable to all degrees of various kinds of burns caused by heat, boiling water, hot steam, hot metal, an explosive substance, strong acid or strong alkali, and provide its production method.

Also, the object of this invention is to provide a burn remedial composition to reduce the treatment period, moderate pain, and exclude toxins, and provide its production method. Compared with the usual and conventional burn treatment, period of 90–100 days, the period is reduced to 3–5 days for second and third degree burns, and upon application, the composition moderates pain of the injury and completely excludes toxins from the injury region to remove toxic symptoms by toxins originated from the region of the injury within 24 hours after its applications.

Another object of the invention is to reduce the production expenses of a burn remedial composition by using natural materials of abalone shell and sesame which are available and are easily obtained.

A further object of the invention is to provide a burn remedial composition which rapidly cures the burns without various kinds of side effects including nausea, emesis, diarrhea, anorexia, vertigo, etc. which can occur when a conventional burn treating agent is applied and thereby reduce a patient's mental, physical, material and time loss, and provide its production method.

Still another object of the invention is to provide a burn remedial composition having epoch-making characteristics and provide its production method. Compared with conventional burn treatment where a burn scar remains in second and third degree burns, the composition completely cures an injury to a normal state without any scar by facilitating and recovering the granulation action in the injury region.

And, the object of the invention is to provide a remedial composition which can be applied to various kinds of external wounds on the skin as well as to burns to rapidly restore the injured area to a normal state with antiphlogistic and analgesic effects.

BEST MODE FOR CARRYING OUT THE INVENTION

This invention mainly consists of two natural materials, abalone shell and sesame. The invention relates to a method of producing a burn remedial composition which comprises mixing abalone shell powder, which is prepared by heating and burning abalone shells in a suitable vessels for heating at a high temperature, and grinding the burned abalone shells to powder with sesame oil which is prepared by extracting sesame in the current method, in any ratio having adequate viscosity for applying to the skin. And, the invention is a burn remedial composition, i.e., a composition of abalone shell powder and sesame oil, having an excellent burn-curing effect which is produced by the above-mentioned method.

In preparing abalone shell powder in the invention, abalone shells are introduced into a suitable vessel for heating which are heated and burned at a temperature higher than 1000° C., preferably higher than 2000° C., and most preferably higher than 3000° C., and the burned abalone shells are ground to powder. In preparing sesame oil in the invention, the conventional method to extract sesame oil from sesame is used. In grinding the burned abalone shells and in mixing of the abalone shell powder and sesame oil, the grinding and the mixing are conducted in any vessel, except stone or metallic vessels, preferably in a wooden vessel. In grinding and mixing processes use of a stone or metallic vessel remarkably reduces the effect of the burn remedial composition. Regarding the mixing ratio, it is advisable to mix in every ratio having adequate viscosity in which the composition of abalone shell powder and sesame oil can be applica to the skin, commonly mixing abalone shell powder of 50–90 weight % of total weight of the compound, preferably of 65–75 weight %, more preferably 70 weight % with the balance of sesame oil to produce burn curing compound. And, if necessary, a conventional pharmaceutical additive is mixed together with the abalone shell powder and sesame oil to aid formulation of a pharmaceutical type of remedial composition.

The burn remedial composition of the invention is applicable to every kind of burn including heat burns and to various kinds of injuries which damage skin tissue.

When applied, the burn remedial composition sticks to the injured region after keeping the injured region clean, and thereafter sterilized gauze and oiled paper are successively applied.

When the burn remedial composition of the invention is applied to the injured region, the antiphlogistic and analgesic effects happen at the moment that the burn remedial composition immediately adheres to the skin by the mutual assistance action of a skin permeating action of sesame oil and a moisture absorbing action, which is an action of abalone shell powder. The remedial composition prevents or eliminates toxicosis within 24 hours after application which can be caused by toxic materials generated from the degraded tissue in the injured region. One of the best effects of the burn remedial composition of the invention is to cure the injury without any scar by helping the regeneration process of injured tissue and renewing rapidly and completely the new skin tissue. As a result, the burn remedial composition has an excellent effect of curing the injury completely within 3-5 days, even a severe burn injury.

Although the invention is described with regard to the following examples, it should be understood that various changes and modifications as would be obvious to one having the ordinary skill in this art may be made without departing from the scope of the invention which is set forth in the claims.

EXAMPLE 1

An adequate quantity of abalone shells were heated at a temperature higher than 3000° C. Then, the ground powder was prepared by grinding the heated abalone shells which were easily ground to a state of fine powder in a wooden vessel. Sesame oil was prepared which was extracted from an adequate amount of sesame by a conventional method.

The prepared abalone shell powder of 70 g was mixed in a wooden vessel with the prepared sesame oil of 30 g to produce a burn remedial composition. The produced burn remedial composition was put into sealed container.

EXAMPLE 2

The burn remedial composition was produced according to the method of example 1, wherein the pharmaceutical additive was added to aid the mixing process when blending the abalone shell powder and sesame oil.

EXAMPLE 3

The burn remedical composition was produced according to the same method of example 1, except that the abalone shell powder was prepared by heating it at a temperature higher than 1000° C. and grinding the burned abalone shells.

EXAMPLE 4

The burn remedical composition was produced according to the same method of example 1, except that the abalone shell powder was prepared by heating it at a temperature higher than 2000° C. and grinding the burned abalone shells.

EXAMPLE 5

Burn remedial compositions were produced by blending the abalone shell powder and sesame oil which were prepared as in each method of Examples 1, 2 and 3, respectively in the following ratio.

| (in weight ratio) | | | | | | | | |
|---|---|---|---|---|---|---|---|---|
| abalone shell powder | 50 | 55 | 60 | 65 | 75 | 80 | 85 | 90 |
| sesame oil | 50 | 45 | 40 | 35 | 25 | 20 | 15 | 10 |

EXAMPLE 6

The burn remedial composition prepared according to Example 1 was applied and adhered to the injured regions of the following patients after keeping the injured regions clean, and thereafter the injury regions were cured after sealing the area with sterilized gauze and sterilized oiled paper. The effects were as follows:

| Patient | | | |
|---|---|---|---|
| | injury region | burn degree | Effect |
| 1 | back of the right hand | third | Injury was completely cured and granulation done after 3 days |
| 2 | legs and arms | second or third | Injury was completely cured and granulation done after 3-5 days |
| 3 | arms | second or third | Injury was completely cured and granulation done after 3-5 days |
| 4 | legs | second | Injury was completely cured and granulation done after 3-5 days |
| 5 | legs and arms | second | Injury was completely cured and granulation done after 3-5 days |
| 6 | legs and arms | third | Injury was completely cured and granulation done after 3-5 days |

In all cases of the above, no side effects appeared, pain was immediately stopped when the burn remedial composition was applied and few scars were observed by the naked eye,

What is claimed is:

1. A burn remedial composition which comprises from 50 to 90% of the total composition of burned abalone shell powder and sesame oil.

2. A burn remedial composition according to claim 1 which further contains a pharmaceutical additive to participate in forming a pharmaceutical type of burn remedy.

3. A burn remedial composition according to claim 1 wherein the abalone shell powder is prepared by heating abalone shells at a temperature higher than 1000° C. and grinding the burned abalone shells.

4. A burn remedial composition according to claim 1 wherein the abalone shell powder is prepared by heating abalone shells at a temperature higher than 2000° C. and grinding the burned abalone shells.

5. A burn remedial composition according to claim 1 wherein the abalone shell powder is prepared by heating abalone shells at a temperature higher than 3000° C. and grinding the burned abalone shells.

6. A burn remedial position according to claim 1 wherein the abalone shell powder is 65–75 weight % of the total amount of the burn remedial composition.

7. A burn remedial composition according to claim 1 wherein the abalone shell powder is 70 weight % of total amount of the burn remedial composition.

8. A method of treatment of burns which comprises applying to a burned area of a patient a therapeutically effective amount of pharmaceutical composition comprising from 50–90% burned abalone shell powder and sesame oil.

* * * * *